United States Patent
Bradshaw et al.

(10) Patent No.: US 9,056,174 B2
(45) Date of Patent: Jun. 16, 2015

(54) MEDICAMENT-CONTAINING DISPENSER PROVIDED WITH A DISPLAY FOR PRESENTING INDICIA TO A USER

(75) Inventors: Douglas Bradshaw, Melbourn Hertfordshire (GB); Oliver Burstall, Melbourn Hertfordshire (GB); Patrick Campbell, Melbourn Hertfordshire (GB); Charles Cooke, Melbourn Hertfordshire (GB); William Cramer, Melbourn Hertfordshire (GB)

(73) Assignee: ASTRAZENECA AB (SE)

(*) Notice: Subject to any disclaimer, the term of this patent is extended or adjusted under 35 U.S.C. 154(b) by 717 days.

(21) Appl. No.: 12/864,345

(22) PCT Filed: Jan. 21, 2009

(86) PCT No.: PCT/SE2009/050056
§ 371 (c)(1),
(2), (4) Date: Oct. 4, 2010

(87) PCT Pub. No.: WO2009/093969
PCT Pub. Date: Jul. 30, 2009

(65) Prior Publication Data
US 2011/0041842 A1   Feb. 24, 2011

Related U.S. Application Data

(60) Provisional application No. 61/022,854, filed on Jan. 23, 2008.

(51) Int. Cl.
*A61M 15/00* (2006.01)
*B67D 7/22* (2010.01)
*B67D 1/00* (2006.01)

(52) U.S. Cl.
CPC ....... *A61M 15/0045* (2013.01); *A61M 15/0065* (2013.01); *A61M 15/009* (2013.01);
(Continued)

(58) Field of Classification Search
None
See application file for complete search history.

(56) References Cited

U.S. PATENT DOCUMENTS 4,969,578 A * 11/1990 Gander et al. ............... 222/131
5,388,572 A    2/1995 Mulhauser et al.
(Continued)

FOREIGN PATENT DOCUMENTS

DE   10 2006 043 637 A1   11/2007
EP          1 366 630 B1    2/2004
(Continued)

OTHER PUBLICATIONS

PCT International Search Report, mailed on Apr. 20, 2009, in PCT/SE2009/050056.
(Continued)

*Primary Examiner* — Tan-Uyen (Jackie) T Ho
*Assistant Examiner* — Eric Bryant
(74) *Attorney, Agent, or Firm* — Finnegan, Henderson, Farabow, Garrett & Dunner, LLP

(57) ABSTRACT

A medicament-containing dispenser, such as an inhaler, comprises an outlet for dispensing medicament, e.g. a mouthpiece or a nasal adaptor. The dispenser also comprises a display for presenting indicia to a user. The dispenser further comprises an outlet cover movable between a first position in which it covers the outlet and a second position in which the outlet is uncovered, wherein, when the outlet cover is in the first position, indicia is visible in the display, and wherein, when the outlet cover is in the second position, indicia is out of sight to the user.

20 Claims, 1 Drawing Sheet

(52) U.S. Cl.
CPC .... *A61M2202/064* (2013.01); *A61M 2205/502* (2013.01); *A61M 2205/582* (2013.01); *A61M 2205/583* (2013.01); *A61M 2205/584* (2013.01); *A61M 15/0026* (2014.02); *A61M 15/0075* (2014.02); *A61M 15/008* (2014.02)

(56) References Cited

U.S. PATENT DOCUMENTS

| | | | | |
|---|---|---|---|---|
| 5,692,492 | A | * 12/1997 | Bruna et al. | 128/200.23 |
| 5,826,571 | A | * 10/1998 | Casper et al. | 128/200.23 |
| 5,921,237 | A | * 7/1999 | Eisele et al. | 128/203.21 |
| 6,006,747 | A | * 12/1999 | Eisele et al. | 128/203.15 |
| 6,148,815 | A | * 11/2000 | Wolf | 128/205.23 |
| 6,422,236 | B1 | 7/2002 | Nilsson et al. | |
| 6,789,497 | B1 | * 9/2004 | Aiken | 116/308 |
| 6,880,722 | B2 | * 4/2005 | Anderson et al. | 221/71 |
| 6,889,690 | B2 | * 5/2005 | Crowder et al. | 128/203.15 |
| 2003/0010337 | A1 | * 1/2003 | Anderson et al. | 128/200.23 |
| 2006/0084908 | A1 | * 4/2006 | Bonney et al. | 604/19 |
| 2006/0185672 | A1 | * 8/2006 | Pinon et al. | 128/203.15 |
| 2007/0267015 | A1 | 11/2007 | Thoemmes et al. | |
| 2008/0001008 | A1 | 1/2008 | Thoemmes et al. | |

FOREIGN PATENT DOCUMENTS

| | | |
|---|---|---|
| GB | 2 242 134 A | 9/1991 |
| WO | WO 02/24269 A1 | 3/2002 |
| WO | WO 2004/009470 A2 | 1/2004 |
| WO | WO 2007/012871 A1 | 2/2007 |
| WO | WO 2007/028992 A1 | 3/2007 |

OTHER PUBLICATIONS

PCT Written Opinion of the International Searching Authority, mailed on Apr. 20, 2009, in PCT/SE2009/050056.

PCT International Preliminary Report on Patentability, issued on Jul. 27, 2010, in PCT/SE2009/050056.

* cited by examiner

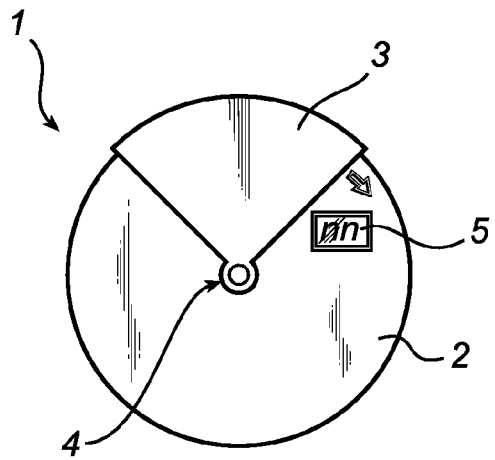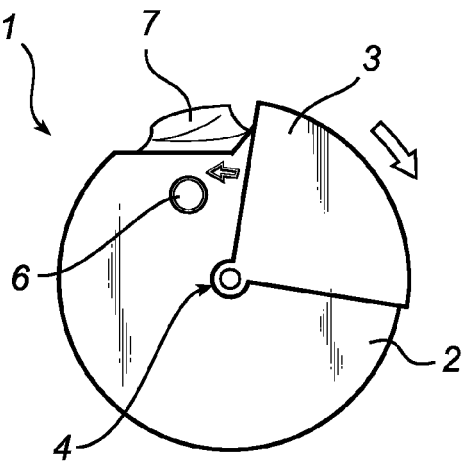
*Fig. 1a*  *Fig. 1b*
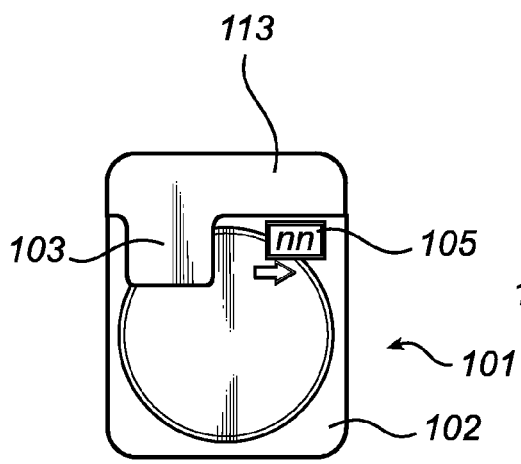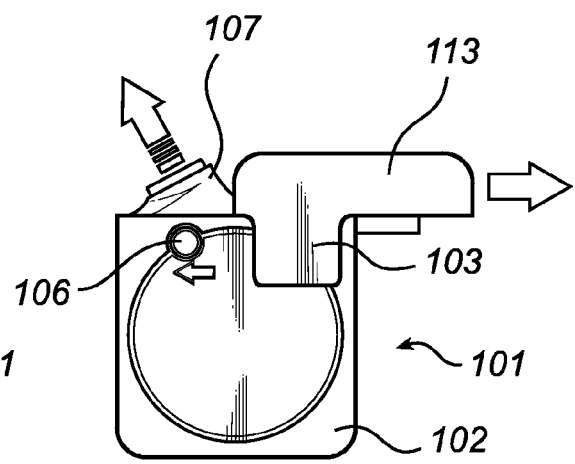
*Fig. 2a*  *Fig. 2b*
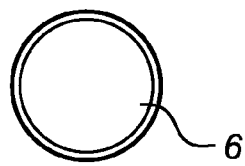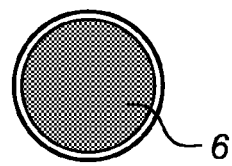
*Fig. 3a*  *Fig. 3b*

MEDICAMENT-CONTAINING DISPENSER PROVIDED WITH A DISPLAY FOR PRESENTING INDICIA TO A USER

This is a U.S. National Phase application of PCT/SE2009/050056, filed on Jan. 21, 2009, which claims the benefit of priority to U.S. Provisional Application No. 61/022,854, filed on Jan. 23, 2008, both of which are incorporated herein by reference in their entireties.

TECHNICAL FIELD

The present invention relates to a medicament-containing dispenser, comprising an outlet for dispensing the medicament and an outlet cover movable between a first position in which it covers the outlet and a second position in which the outlet is uncovered.

BACKGROUND OF THE INVENTION

There are various types of medicament-containing dispensers, such as packages or devices for dispensing tablets, salves or inhalable substances, to mention a few. Some dispensers are provided with a counting device to keep a user informed of the number of doses dispensed or remaining in the dispenser. For instance, inhalers are often provided with a counting device to show how many inhalable doses have been dispensed or remain to be dispensed.

U.S. Pat. No. 5,388,572 illustrates a dispenser in the form of a medicament inhaler. In one embodiment, the inhaler comprises an opening through which a user can view indicia indicating the number of the dose next to be dispensed, and another opening which can be used to view indicia comprising the word "READY". The user inhales the medicament through an outlet in the form of a mouthpiece. A movable cover is provided for the mouthpiece.

Similarly, other types of dispensers have outlets for enabling a user to access the medicament. The outlet may be in the form of a simple opening in a housing, a nozzle, a nasal adaptor, etc. Like for the above mentioned inhaler, also the other types of dispensers are often provided with an outlet cover to reduce the risk of contamination or unwanted matter adhering to or entering through the outlet. Unfortunately, for various reasons, such as absent-mindedness, carelessness or just pure ignorance of the importance of covering the outlet, some users do not always cover the outlet after having used the dispenser.

SUMMARY OF THE INVENTION

An object of the invention is to provide a dispenser which promotes a different user behaviour so as to reduce the risk of users not covering a dispenser outlet. This object is accomplished by a medicament-containing dispenser having the characteristics defined in the accompanied independent claim.

The invention is based on the insight that by displaying information which is relevant to the user only when a dispenser outlet is covered, there will be an incentive to the user to cover the outlet. By making it clearer to the user that the dispenser has two separate states: a storing state and a dispensing state, the user will be more likely to cover the outlet after having dispensed a dose of medicament from the dispenser.

According to an aspect of the invention, a medicament-containing dispenser is provided. The dispenser comprises an outlet for dispensing the medicament, a display for presenting indicia to a user, and an outlet cover movable between a first position in which it covers the outlet and a second position in which the outlet is uncovered. When the outlet is cover is in said first position, indicia is visible in said display and when the outlet cover is in said second position, indicia is out of view to the user. Thus, by only presenting the indicia to the user when the outlet cover actually covers the outlet, the user will have an incentive to return the cover to its first position in order for the user to receive the information obtainable by viewing the indicia.

The indicia may represent various types of information, such as a dose count, a state of the dispenser, date or time indication, or any other memory or compliance aid-related information. The indicia may be in the form of one or more signs, symbols, letters, numbers, colour codes, patterns, braille etc. The indicia may be presented mechanically, e.g. on a printed disk, gear wheel, strip etc., through a display opening or window or by other suitably display means. Alternatively, the indicia may be electronically presented on e.g. a liquid crystal display (LCD) or by other suitable electronic display means. In either the mechanical or the electronical alternative, the indicia may be changeable to provide different information in dependence of the present situation. Thus, it is to be understood that a display can be embodied in various ways in order to provide a visual representation of information.

There are various ways of making indicia visible in only one of the positions of the outlet cover and having it out of view to the user in the other position of the outlet cover. To arrange the indicia out of view to the user, the dispenser may comprise a concealing means, in accordance with at least one example embodiment of the invention. A concealing means may either comprise a physical/mechanical feature which places an opaque or some other non-transparent structure in front of the indicia or moves the indicia behind such a structure, or it may comprise an electronic feature which through a circuit switches off an electronically presented indicia. Furthermore, the concealing means may be designed to conceal the actual indicia while maintaining the display in sight of the user. For instance, if the dispenser has a housing which comprises a display opening or window for presenting indicia inside the housing, the concealing means may be in the form of a covering sheet which slides under the display opening or window to cover the indicia, or the concealing means may be the actual housing wherein movement of the indicia away from the display opening/window hides the indicia behind the housing wall.

An alternative to just concealing the indicia is to conceal the actual display presenting the indicia. Thus, according to at least one example embodiment of the invention, the concealing means is adapted to conceal the display.

Although there are various ways of concealing the display, according to at least one example embodiment of the invention, the concealing means comprises the outlet cover, wherein the display is concealed by the outlet cover when the outlet cover is in the second position. As an alternative to having the outlet cover concealing the display, it would be conceivable to have some other concealing component which is connected to the outlet cover or affected by its movement.

The dispenser may have more than one display for presenting indicia to a user. In such case several alternatives are conceivable. One alternative is that for all the displays the indicia is only visible when the outlet cover is in the first position, i.e. covering the outlet, while no indicia is visible in the displays when the outlet cover is in the second position. A second alternative is that in some (one or more) of the displays the indicia is only visible when the outlet cover is in the first position, while in the rest of the displays the indicia is visible regardless of the position of the outlet cover. Thus, the user would still have to close the cover to be able to view such indicia which is only visible when the outlet cover is in the first position. A third alternative is that, when the outlet cover is in the first position, the user will be able to view indicia in some of the displays but not in others, and when, the outlet cover is in the second position, the indicia which was not viewable becomes visible and vice versa.

The just-mentioned third alternative is reflected in at least one example embodiment of the invention, wherein the dispenser comprises a first display for presenting indicia to a user and also a second display for presenting indicia to the user, wherein, when said outlet cover is in said first position, indicia is only visible in the first display, and wherein, when said outlet cover is in said second position, indicia is only visible in the second display. Suitably, the information provided in the second display is only relevant to the user when the user wishes to take the medicament, thus not providing the user with an incentive to uncover the outlet without due cause. For instance, such information may relate to the dispensing state of the dispenser.

It should be noted that the previously described concealing means in connection with a dispenser having one display, is also usable in connection with a dispenser having several displays. For instance, according to at least one example embodiment, when said outlet cover is in said first position, the first display is visible and the second display is concealed by said concealing means, and, when said outlet cover is in said second position, the second display is visible and the first display is concealed by said concealing means. Similarly, according to another example embodiment, said concealing means comprises the outlet cover, wherein said first and second displays are concealed by the outlet cover when the outlet cover is in the second and first positions, respectively. In this latter example, the same portion of the outlet cover may be used for alternatingly concealing the displays by moving that portion from one display to another when the outlet cover is moved between its positions. Alternatively, there may be two or more different portions of the outlet cover for concealing a respective display.

As mentioned previously, the indicia may represent various types of information. In the case of a dispenser having two displays, according to at least one example embodiment, the first display presents indicia indicating the number of doses that has been dispensed or remains to be dispensed from the dispenser.

According to at least one example embodiment, the second display presents indicia indicating the current dispensing state of the dispenser. The dispenser may be variable between at least the following two dispensing states: a dose is ready for dispensing and a dose has been correctly dispensed. If a dose has not been correctly dispensed the indicia may simply continue to indicate that a dose is ready for dispensing. Optionally, a third dispensing state may be provided: a dose has been incorrectly dispensed. For instance, the dispenser may have indicia in the form of a yellow symbol indicating ready, and when a dose has been correctly dispensed a green symbol is shown, and if the dose was incorrectly dispensed a red symbol is shown. Naturally, other indicia such as icons or printed text could be used, e.g.: "ready", "dose taken" and "failed", respectively. Apart from the above-mentioned dispensing states, the dispenser also has the storage state in which the outlet cover covers the outlet.

According to at least one example embodiment, the first display has a different geometrical shape compared to the second display. This makes it more apparent to the user that there are actually two displays, even though they (or there indicia) are alternatingly concealed, thus only showing one of them at a time. Consequently, it will be a further reminder to the user that there is a storage state and will provide an incentive to the user to return the outlet cover to the first position to cover the outlet. There are, of course, other alternatives for making the displays different, such as various tactile differences or different indicia designs etc.

The outlet cover may be movable between said first and second positions in various ways. One alternative is a sliding movement. Another alternative is a rotating movement. The movement path or pattern may suitably adapted to the design of the dispenser.

According to at least one example embodiment, the medicament-containing dispenser is in the form of an inhaler, wherein said outlet is a mouthpiece or nasal adaptor through which a user is enabled to inhale the medicament. However, the previously described features and other example embodiments are equally conceivable and applicable in any suitable type of dispenser, such as packages or devices for tablets/capsules, liquid medication or salves. Likewise, there is no limitation to a specific kind of inhaler. On the contrary, the inventive idea applicable to dry powder inhalers (DPIs) as well as to pressurised metered dose inhalers (pMDIs), small volume nebulisers (SVNs) and various types of add-ons. For DPIs the powder may either be contained in a bulk and be metered for each inhalation, or the powder may be contained in discrete dose enclosures such as blisters or sealed cavities.

Furthermore, in case of the dispenser being in the form of an inhaler, it may contain various drugs and/or bioactive agents to be inhaled.

The bioactive agent may be selected from any therapeutic or diagnostic agent. For example it may be from the group of antiallergics, bronchodilators, bronchoconsitrictors, pulmonary lung surfactants, analgesics, antibiotics, leukotrine inhibitors or antagonists, anticholinergics, mast cell inhibitors, antihistamines, antiinflammatories, antineoplastics, anaesthetics, anti-tuberculars, imaging agents, cardiovascular agents, enzymes, steroids, genetic material, viral vectors, antisense agents, proteins, peptides and combinations is thereof.

Examples of specific drugs which can be incorporated in the dispenser according to the invention include mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, Symbicort™ (budesonide and formoterol), terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propanesulphonamide, hydrochloride. All of the above compounds can be in free base form or as pharmaceutically acceptable salts as known in the art.

Combinations of drugs may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

BRIEF DESCRIPTION OF THE DRAWINGS

FIGS. 1a-1b illustrate a medicament-containing dispenser according to an example embodiment of the invention.

FIGS. 2*a*-2*b* illustrate a medicament-containing dispenser according to another example embodiment of the invention.

FIGS. 3*a*-3*b* illustrate a display having indicia indicating different dispensing states.

DETAILED DESCRIPTION OF THE DRAWINGS

Although a medicament-containing dispenser according to the invention may be embodied in various devices and packages and for various purposes, the dispensers in the drawings have been illustrated in the form of inhalers. Furthermore, although a medicament-containing dispenser according to the invention may have just one display or more than two, for illustrative purposes, the dispensers in the drawings have been provided with two displays.

FIGS. 1*a*-1*b* illustrate a medicament-containing dispenser according to an example embodiment of the invention. The dispenser is in the form of an inhaler 1 containing inhalable medicament. The inhaler 1 comprises a generally circular main body or housing 2, in which powdered medicament is contained either in bulk or in discrete enclosures, or in which a pressurized medicament is contained and is dispensable as an aerosol. A concealing means 3 in the form of a mouthpiece cover 3 is adapted to rotate relative to the housing 2. The mouthpiece cover 3 is hinged to a boss 4 provided centrally on the housing 2 and is adapted to perform a rotational movement by pivoting around the boss 4. The mouthpiece cover 3 can rotate between two positions, which may be provided with end stops (not shown) for preventing further rotation. The first position is illustrated in FIG. 1*a*. In this first position, a first display 5 is visible while the mouthpiece cover 3 conceals a second display 6. Also, in this first position, next to the first display 5, an arrow is provided on the housing 2 to inform the user which way to move the mouthpiece cover 3. Furthermore, in this first position, the mouthpiece cover 3 covers a mouthpiece 7 through which a user may inhale the medicament. Thus, FIG. 1*a* illustrates a storing state of the inhaler 1. In order to use the inhaler 1, the user rotates the mouthpiece cover 3 (in this example clockwise, as illustrated by the large arrow in FIG. 1*b*) in order to expose the mouthpiece 7 which is illustrated in FIG. 1*b*. Thus, FIG. 1*b* illustrates the second position of the mouthpiece cover 3. In this second position, the mouthpiece cover 3 conceals the first display, while the second display 6 is visible. Next to the second display 6, an arrow provided on the housing 2 informs the user which way to move the mouthpiece cover 3. Thus, only one display at a time is visible. Likewise, only one directional arrow at a time is visible.

In the illustrated example, the first display 5 presents indicia indicating the number of doses dispensed or remaining to be dispensed from the inhaler 1, while the second display 6 may suitably indicate the dispensing state of the inhaler 1, as is further discussed with reference to FIGS. 3*a*-3*b* which illustrate the second display 6 having indicia indicating different dispensing states. When a user has exposed the mouthpiece 7 by moving the mouthpiece cover 3, the second display 6 indicates that the inhaler 1 is ready for inhalation. For instance, this may be represented by a first colour indicia as exemplified in FIG. 3*a*. After completed inhalation, a second colour indicia will appear in the second display 6 as exemplified in FIG. 3*b*. It would be conceivable to also have a third colour indicia to indicate a failed inhalation attempt or incorrect dispensing. Of course, other types of indicia are usable instead of colours, e.g. different icons.

After completed or attempted inhalation, the user returns the mouthpiece cover 3 to its original first position shown in FIG. 1*a* in order to see the dose count in the first display 5. Thus, by hiding the dose count display 5 when the mouthpiece cover 3 is removed from the mouthpiece, there will be an incentive to the user to return the mouthpiece cover 3.

FIGS. 2*a*-2*b* illustrate a medicament-containing dispenser according to another example embodiment of the invention. Also in this example, the dispenser is in the form of an inhaler 101. The housing 102 is generally rectangular or square. A concealing means is provided in the form of a projecting portion 103 of a mouthpiece cover 113. Similarly to the other illustrated example embodiment, there is a first display 105 for providing a dose count, and a second display 106 for providing information related to the dispensing state of the inhaler 101. In FIG. 2*a*, the mouthpiece cover 113 is in its first position, wherein the projecting portion 103 conceals the second display 106 while the first display 105 is visible to a user. In order to inhale, the user slides the mouthpiece cover 113 linearly as indicated by the arrow on the right hand side in FIG. 2*b* (an arrow is provided next to the first display 105 to inform the user in which direction to slide the mouthpiece cover).

The movement of the mouthpiece cover 113 to this second position results in a mouthpiece 107 exiting from the housing 102 as illustrated by the broken arrow. Thus, in this example embodiment, in the storage state shown in FIG. 2*a*, the mouthpiece 107 is kept inside the housing 102 by the mouthpiece cover 113 and is biased to exit when the mouthpiece cover 113 is removed as shown in FIG. 2*b*. Also shown in FIG. 2*b*, the movement of the mouthpiece cover 113 has resulted in that the concealing projecting portion 103 has moved to conceal the first display 105 and to make the second display 106 visible. The first and second displays in the example shown in FIGS. 2*a*-2*b* may have the same characteristics as those shown in FIGS. 1*a*-1*b*.

The above example embodiments are not to be construed in any limiting way. It should be understood that the inventive idea may be used without the second display 6, 106. It should also be understood that the inventive idea is applicable to other types of dispensing devices from which medicament is picked out, squeezed, ejected or dispensed in any other suitable way.

The invention claimed is:

1. A medicament-containing dispenser, comprising:
   an outlet for dispensing the medicament;
   a display for presenting an indicia to a user, the indicia representing dosing information;
   an outlet cover movable between a first position in which the outlet cover covers the outlet and a second position in which the outlet is uncovered;
   a concealing member adapted to conceal the display;
   wherein, when said outlet cover is in said first position, the indicia is visible in said display; and
   wherein, when said outlet cover is in said second position, the indicia is out of view to the user.

2. The medicament-containing dispenser as claimed in claim 1, further comprising a circuit configured to disable the display, wherein the display electronically presents the indicia.

3. The medicament-containing dispenser as claimed in claim 1, wherein said concealing member comprises the outlet cover, wherein said display is concealed by the outlet cover when the outlet cover is in the second position.

4. The medicament-containing dispenser as claimed in claim 3, wherein said display is a first display and the indicia is a first indicia, the medicament-containing dispenser further comprising a second display for presenting a second indicia to a user, wherein, when said outlet cover is in said first position, the first indicia is visible in the first display and the second indicia is not visible in the second display, and wherein, when said outlet cover is in said second position, the second indicia is visible in the second display and the first indicia is not visible in the first display.

5. The medicament-containing dispenser as claimed in claim 4, wherein, when said outlet cover is in said first position, the first display is visible and the second display is concealed by said concealing member, and wherein, when said outlet cover is in said second position, the second display is visible and the first display is concealed by said concealing member.

6. The medicament-containing dispenser as claimed in claim 5, wherein said concealing member comprises the outlet cover, wherein said first and second displays are concealed by the outlet cover when the outlet cover is in the second and first positions, respectively.

7. The medicament-containing dispenser as claimed in claim 4, wherein the first display presents the first indicia indicating a number of doses that have been dispensed or remain to be dispensed from the medicament-containing dispenser.

8. The medicament-containing dispenser as claimed in claim 7, wherein the second display presents the second indicia indicating a current dispensing state of the medicament-containing dispenser.

9. The medicament-containing dispenser as claimed in claim 8, wherein the medicament-containing dispenser is variable between at least two of the following dispensing states:
  a dose is ready for dispensing, and
  a dose has been correctly dispensed, and
  a dose has been incorrectly dispensed.

10. The medicament-containing dispenser as claimed in claim 1, wherein the first display has a different geometrical shape compared to the second display.

11. The medicament-containing dispenser as claimed in claim 1, wherein the outlet cover is slidable between said first and second positions.

12. The medicament-containing dispenser as claimed in claim 1, wherein the outlet cover is rotatable between said first and second positions.

13. The medicament-containing dispenser as claimed in claim 4, further comprising a housing, wherein at least one of said first and second displays comprises at least one of an opening and a window in the housing through which the first indicia and the second indicia are presentable.

14. The medicament-containing dispenser as claimed in claim 1, wherein at least one of the first indicia presented by the first display and the second indicia presented by the second display is mechanically changeable.

15. The medicament-containing dispenser as claimed in claim 1, wherein the medicament-containing dispenser is an inhaler, wherein said outlet includes at least one of a mouthpiece and a nasal adaptor through which a user is enabled to inhale the medicament.

16. The medicament-containing dispenser as claimed in claim 2, wherein said display is a first display and the indicia is a first indicia, the medicament-containing dispenser further comprising a second display for presenting a second indicia to a user, wherein the circuit is further configured to
  enable display of the first indicia in the first display and disable display of the second indicia in the second display when said outlet cover is in said first position, and
  enable display of the second indicia in the second display and disable display of the first indicia in the first display when said outlet cover is in said second position.

17. The medicament-containing dispenser as claimed in claim 16, wherein the first display presents the first indicia indicating a number of doses that has been dispensed or remains to be dispensed from the medicament-containing dispenser.

18. The medicament-containing dispenser as claimed in claim 17, wherein the second display presents the second indicia indicating a current dispensing state of the medicament-containing dispenser.

19. The medicament-containing dispenser as claimed in claim 18, wherein the dispenser is variable between at least two of the following dispensing states:
  a dose is ready for dispensing, and
  a dose has been correctly dispensed, and
  a dose has been incorrectly dispensed.

20. The medicament-containing dispenser as claimed in claim 1, wherein the outlet cover is pivotable between said first and second positions.

* * * * *